United States Patent
Liu et al.

(10) Patent No.: US 9,778,217 B2
(45) Date of Patent: Oct. 3, 2017

(54) EXPLOSION-PROOF MINIATURIZED COMBUSTIBLE GAS SENSOR

(71) Applicant: RAE Systems (Shanghai) Inc., Shanghai (CN)

(72) Inventors: Fuxia Liu, Shanghai (CN); Aimin Su, Shanghai (CN)

(73) Assignee: RAE SYSTEMS (SHANGHAI) INC., Shanghai (CN)

( * ) Notice: Subject to any disclaimer, the term of this patent is extended or adjusted under 35 U.S.C. 154(b) by 91 days.

(21) Appl. No.: 14/432,092

(22) PCT Filed: Sep. 26, 2013

(86) PCT No.: PCT/CN2013/084260
§ 371 (c)(1),
(2) Date: Mar. 27, 2015

(87) PCT Pub. No.: WO2014/048335
PCT Pub. Date: Apr. 3, 2014

(65) Prior Publication Data
US 2015/0253272 A1   Sep. 10, 2015

(30) Foreign Application Priority Data

Sep. 28, 2012  (CN) .......................... 2012 1 0367286
Sep. 28, 2012  (CN) ...................... 2012 2 0510916 U

(51) Int. Cl.
*G01N 27/16* (2006.01)
*G01N 27/04* (2006.01)
*G01N 33/00* (2006.01)

(52) U.S. Cl.
CPC .......... *G01N 27/16* (2013.01); *G01N 27/045* (2013.01); *G01N 33/0009* (2013.01)

(58) Field of Classification Search
CPC .. G01N 27/16; G01N 27/045; G01N 27/0016; G01N 33/0009; G01N 33/0004
(Continued)

(56) References Cited

U.S. PATENT DOCUMENTS 4,352,099 A * 9/1982 Christen .............. G08B 17/117
340/633
5,601,693 A * 2/1997 Davies ................... G01N 27/16
204/400

(Continued)

FOREIGN PATENT DOCUMENTS

CN          1342263 A       3/2002
CN       200989890 Y       12/2007
(Continued)

OTHER PUBLICATIONS

PCT/CN2013/084260, PCT International Search Report, dated Jan. 9, 2014, 8 pages.
(Continued)

*Primary Examiner* — Natalie Huls
*Assistant Examiner* — Monica S Young
(74) *Attorney, Agent, or Firm* — Conley Rose, P.C.; Kristin Jordan Harkins

(57) ABSTRACT

The present invention provides an explosion-proof miniaturized combustible gas sensor, comprising: a metal casing having an accommodation space therein; a wire mesh, a vertical surface perpendicular to a side surface where the wire mesh is located and the other side surface opposite thereto being used as a transfer surface of the combustible gas; a heat insulation module embedded in the metal casing; a detection module sensitive to a combustible gas; a compensation module insensitive to a combustible gas and matching the detection module; where the detection module has a higher catalytic combustion activity than the compen- (Continued)

sation module; a sealant, where a bonding length of the sealant in the accommodation space of the metal casing is used as an effective bonding surface, and the effective bonding surface is perpendicular to the transfer surface. The present invention has the advantages of a miniaturized size, good explosion-proof property and reliable performance.

20 Claims, 2 Drawing Sheets

(58) Field of Classification Search
USPC ........................................................ 73/23.31
See application file for complete search history.

(56) References Cited

U.S. PATENT DOCUMENTS

| | | | | |
|---|---|---|---|---|
| 5,710,475 | A * | 1/1998 | Irwin | B32B 27/18 174/120 SR |
| 5,874,737 | A * | 2/1999 | Bytyn | G01N 21/3504 250/338.5 |
| 6,202,472 | B1 * | 3/2001 | Wezurek | G01N 33/0009 73/23.31 |
| 6,344,174 | B1 * | 2/2002 | Miller | G01N 27/16 422/90 |
| 7,426,850 | B2 | 9/2008 | Takahashi et al. | |
| 2002/0014411 | A1 * | 2/2002 | Shirai | C03C 3/066 204/424 |
| 2003/0180445 | A1 * | 9/2003 | Wang | C23C 4/02 427/58 |
| 2004/0208789 | A1 | 10/2004 | Miller et al. | |
| 2005/0217370 | A1 * | 10/2005 | Takahashi | G01N 33/0009 73/431 |
| 2006/0243029 | A1 * | 11/2006 | Lange | G01N 25/50 73/31.05 |
| 2009/0016934 | A1 * | 1/2009 | Schlichte | G01N 27/16 422/94 |
| 2009/0035184 | A1 * | 2/2009 | Koda | G01N 27/16 422/94 |
| 2009/0223278 | A1 * | 9/2009 | Cowburn | G01N 27/16 73/23.31 |
| 2009/0324449 | A1 * | 12/2009 | Kira | G01N 27/16 422/96 |
| 2010/0192675 | A1 * | 8/2010 | Schlichte | G01N 27/16 73/31.06 |
| 2011/0094880 | A1 * | 4/2011 | Schlichte | G01N 27/16 204/400 |
| 2012/0291522 | A1 * | 11/2012 | Tsukabayashi | G01N 27/16 73/23.21 |

FOREIGN PATENT DOCUMENTS

| | | |
|---|---|---|
| CN | 102053135 A | 5/2011 |
| CN | 102879435 A | 1/2013 |
| CN | 202886313 U | 4/2013 |
| GB | 239716 A | 3/1999 |
| GB | 2437984 A | 11/2007 |
| JP | 2000065783 A | 3/2000 |

OTHER PUBLICATIONS

Europe Patent Application No. 13841122.8, Extended European Search Report, dated Mar. 3, 2016, 10 pages.
PCT/CN2013/084260, PCT Written Opinion of the International Searching Authority, dated Jan. 9, 2014, 13 pages.
PCT/CN2013/084260, PCT International Preliminary Report on Patentability, dated Mar. 31, 2015, 6 pages.
Europe Patent Application No. 13841122.8, Examination Report dated Jan. 4, 2017, 8 pages.

* cited by examiner

EXPLOSION-PROOF MINIATURIZED COMBUSTIBLE GAS SENSOR

CROSS-REFERENCE TO RELATED APPLICATIONS

This application is a filing under 35 U.S.C. 371 as the National Stage of International Application No. PCT/CN2013/084260 entitled EXPLOSION-PROOF MINIATURIZED COMBUSTIBLE GAS SENSOR and filed Sep. 26, 2013, which claims priority to China Patent Application No. 201210367286.8 entitled SMALL-SIZE EXPLOSION-PROOF SENSOR FOR INFLAMMABLE GAS filed Sep. 28, 2012 with the China State Intellectual Property Office of the P.R.C. (SIPO) and to China Patent Application No. 201220510916.8 entitled EXPLOSION-PROOF TYPE MINIATURIZED COMBUSTIBLE GAS SENSOR filed Sep. 28, 2012 with the China State Intellectual Property Office of the P.R.C. (SIPO), such that the present application also claims priority to China Patent Application No. 201210367286.8 and China Patent Application No. 201220510916.8; all of which are incorporated herein by reference.

TECHNICAL FIELD

The present invention relates to a small and portable combustible gas detector having a strong explosion-proof capability.

BACKGROUND OF THE INVENTION

In order to prevent explosion of a combustible gas after reaching a certain concentration to ensure production safety, a combustible gas detecting and alerting device is usually arranged in a factory or facility wherein a combustible gas is produced and used. A major constituent of such combustible gas detecting and alerting device is a combustible gas detector. Current combustible gas detectors mainly consist of a gas sensitive element, a gas sensitive element fixing sleeve, a rain cover and a cable entry means.

Currently, a combustible gas detector of such a structure is not secure in design, thus, when applied in a combustible gas environment, there is a risk of creating a detonation in the surrounding environment, and providing a more explosion proof design often cannot be satisfied. Thus, an explosion-proof encapsulation is required. A traditional method to form an explosion-proof encapsulation for a combustible gas detector is to encapsulate a catalytic bead in a stainless steel casing, which has a flame catching and extinguishing sintered sheet, and the end of the casing is poured with epoxy to be leak-proof. In accordance with the standard for explosion-proof authentication in Europe and North America, it is required that for any explosion-proof casing, if sealed using a sealant, a bonding length between the sealant and the casing in the sealing direction shall be no less than 3 mm. Besides, the design of sealing with a sealant requires a sufficient size so that the explosion proof effect can be ensured. Thus, the size of a traditional design is usually large, and a small and portable combustible gas detector cannot be realized.

Usually, measurement means of a combustible gas detector include: a thermal conductivity detector, an infrared detector, and catalytic combustion detection, etc. These detection means mostly adopt the manner of heat measurement, that is, detecting a combustible gas by influence on the temperature or heat of a sensitive element caused by flow, infrared absorption or combustion of a combustible gas. However, according to common knowledge, any detection involving heat measurement will necessarily be influenced by a change in temperature of the ambient environment. Thus, a heat-measuring sensor usually requires a reference detector or a reference element for canceling influence on the measurement of the detecting element caused by environmental factors such as temperature, humidity, pressure, airflow, etc. Obviously, the reference element needs to be infinitely consistent with the detecting element in term of several factors such as temperature, humidity, pressure and airflow, etc. such that a maximal compensation effect can be achieved. Unfortunately, the compensation effect of reference elements in current combustible gas detectors, especially catalytic combustion or thermal conductivity sensors, are far from ideal due to the product design and the less advanced production process. That is to say, currently, combustible gas detectors manufactured by most of the manufacturers still have significant effects of temperature, humidity, pressure and airflow etc. although undergoing compensation by a reference element.

SUMMARY OF THE INVENTION

The purpose of the present invention is to provide an explosion-proof miniaturized combustible gas sensor to solve the problems such as limitation in the size of a combustible gas detector, difficulty in miniaturization, and poor compensation, etc.

In order to solve the aforesaid problems as well as other problems, the present invention provides an explosion-proof miniaturized combustible gas sensor, comprising: a metal casing having an accommodation space therein; a wire mesh provided on a side surface of said metal casing and in connection with said accommodation space for gas exchange such that a gas under detection is transferred into said metal casing via said wire mesh; a vertical surface perpendicular to said side surface where the wire mesh is located and the other side surface opposite thereto being used as a transfer surface of the combustible gas; a heat insulation module embedded in the accommodation space of said metal casing; a detection module sensitive to the combustible gas; a compensation module insensitive to the combustible gas and matching said detection module; wherein said detection module has a higher combustible gas detection sensitivity than said compensation module; a sealant for configuring said heat insulation module, detection module and compensation module in the accommodation space of said metal casing; wherein a bonding length of said sealant in said accommodation space of said metal casing is used as an effective bonding surface, wherein said effective bonding surface is perpendicular to said transfer surface of the combustible gas.

Optionally, said detection module comprises: a detection element assembled in said heat insulation module and a pair of detection pins connected to two ends of said detection element respectively and extending via said sealant from a side surface of said metal casing; and said compensation module comprises: a compensation element assembled in said heat insulation module and a pair of compensation pins connected to two ends of said compensation element respectively and extending via said sealant from a side surface of said metal casing.

Optionally, said detection module and said compensation module are fixed in said sensor via a fixing support, or said detection module and said compensation module are coupled, nested or locked to each other to fix each other, thereby being fixed in the sensor.

Optionally, said detection module comprises: a detection element assembled in said heat insulation module and a pair of detection pins connected to two ends of said detection element respectively and extending via said sealant from a side surface of said metal casing; and said compensation module comprises: a compensation element assembled in said heat insulation module and a pair of compensation pins connected to two ends of said compensation element respectively and extending via said sealant from a side surface of said metal casing.

Optionally, the compensation element in said compensation module has a lower combustible gas detection sensitivity, or even has no combustible gas detection sensitivity as compared with the detection element in said detection module.

Optionally, the compensation module matching said detection module comprises a resistance of said compensation module matching a resistance of said detection module; in the range of −40° C. to +70° C., where a ratio between the resistance of said detection module and the resistance of said compensation module ranges from 0.975 to 1.013.

Optionally, said detection module further comprises a detection pin frame for supporting said pair of detection pins, said compensation module further comprises a compensation pin frame for supporting said pair of compensation pins.

Optionally, said heat insulation module is composed of a thermal resistance material, where a thermal conductivity coefficient of said thermal resistance material is smaller than 0.6 w/(m·K), and said thermal resistance material is of a gas state, a liquid state or a solid state.

Optionally, a seam allowance slot in contact with said sealant is provided on an inner wall of said metal casing.

Optionally, a linear expansion coefficient of said sealant is $10^{-6}$ in./in./° C.~$10^{-5}$ in./in./° C.

Optionally, a surface of said metal casing includes an opening, and said detection module, compensation module and heat insulation module are placed into the accommodation space of said metal casing via said opening, thereafter said opening is sealed with said sealant.

The explosion-proof miniaturized combustible gas sensor provided by the present invention comprises a metal casing, a wire mesh arranged on said metal casing, a heat insulation module embedded in said metal casing, a detection module and a compensation assembled in said heat insulation module and a sealant. Such a structure has the following advantages:

1. The transfer surface of the combustible gas is perpendicular to the effective bonding surface of the sealant such that the bonding length required by the explosion-proof authentication (e.g. at least 3 mm) does not occupy the height of the sensor, thus the overall height of the sensor can be reduced. Besides, since the detection pins and the compensation pins configured for the detection module and compensation module, respectively, extend from a side surface of the metal casing, as compared with the prior art of the pins extending from the front surface or the bottom surface, the overall thickness of the product can be reduced greatly, thereby realizing the miniaturization of the product; furthermore, arranging a heat insulation module in the surrounding of the detection module and the compensation module can prevent heat loss due to a relative big gap between the two modules and the metal casing, in this way, the overall size of the sensor can be further reduced.

2. The present invention provides a detection module sensitive to a combustible gas and a compensation module insensitive to a combustible gas, and said detection module has a higher combustible gas detection sensitivity than said compensation module; wherein the so-called combustible gas detection sensitivity refers to a change rate of a physical quantity or a chemical quantity indicating a change of a combustible gas along with a change of concentration of a combustible gas. Particularly, the detection module and the compensation module are made into two independent modules and a pairing and matching operation is performed to the two modules during manufacturing, encapsulation is performed after the matching (e.g. resistance matching to make the resistance values of the two equal or have a very small difference), thereby avoiding the problem of poor compensation and enabling said compensation module to compensate influence on a signal of said detection module caused by ambient temperature, humidity, pressure and airflow, etc.

3. A linear expansion coefficient of said sealant is $10^{-6}$ in./in./° C.~$10^{-5}$ in./in./° C., which is close to a linear expansion coefficient of stainless steel, thus, even after a one-month-long extreme high and low temperature cycle as prescribed in the explosion-proof authentication standard, a sufficient bonding strength between the sealant and the stainless casing can be maintained, which is sufficient to resist the subsequent static hydraulic pressure test of as high as 4 MPa.

| | |
|---|---|
| 1 | Combustible gas concentration detection system |
| 11 | Metal casing |
| 13 | Wire mesh |
| 15 | Heat insulation module |
| 14 | Clip |
| 17 | Detection module |
| 171 | Detection element |
| 173 | Detection pin |
| 175 | Detection pin frame |
| 16 | Fixing frame |
| 19 | Compensation module |
| 191 | Compensation element |
| 193 | Compensation pin |
| 195 | Compensation pin frame |

DETAILED DESCRIPTION OF THE PRESENT INVENTION

The inventors of the present invention discovered that current combustible gas sensors have problems such as limitation in size, difficulty in miniaturization and poor compensation, etc. Thus, the inventors of the present invention have improved the prior art and propose a novel explosion-proof miniaturized combustible gas sensor, wherein the gas transfer surface is perpendicular to an effective bonding surface of a sealant, and respective pins extend from a side surface of a metal casing, thereby reducing the overall thickness of a product and allowing for miniaturization; further, the problem of poor compensation is avoided by manufacturing a detection module and a compensation module into two independent and matching modules.

The implemention of the present invention is explained with the following specific embodiments. Those skilled in the art can easily learn other advantages and effects of the present invention through the contents disclosed in the Description. The present invention can be implemented or applied through other different specific implementations, and the details in the present Description can be based on different opinions and applications and modifications and changes can be made without deviation from the spirit and principle of the present invention.

It should be noted that the structure, proportion and size, etc shown in the figures of the Description of an explosion-proof miniaturized combustible gas sensor according to the present invention are all used in coordination with the contents disclosed in the Description for reading and understanding of those skilled in the art, but are not used as limiting conditions under which the present invention can be implemented and do not have substantive meaning technically. Any modification to the structure, change in the proportional relation or adjustment of the size, if not affecting the effect of and purpose achieved by the present invention, still fall within the coverage scope of the technical contents disclosed by the present invention. In the meanwhile, the terms "upper", "lower", "left", "right", "middle" and "a" used in this Description are only for clarity of description and not for limiting the scope of implementation of the present invention, the change or adjustment of the relative relationship thereof without changing the technical content in substance, should be deemed as falling within the implementable scope of the present invention.

Figure 1:
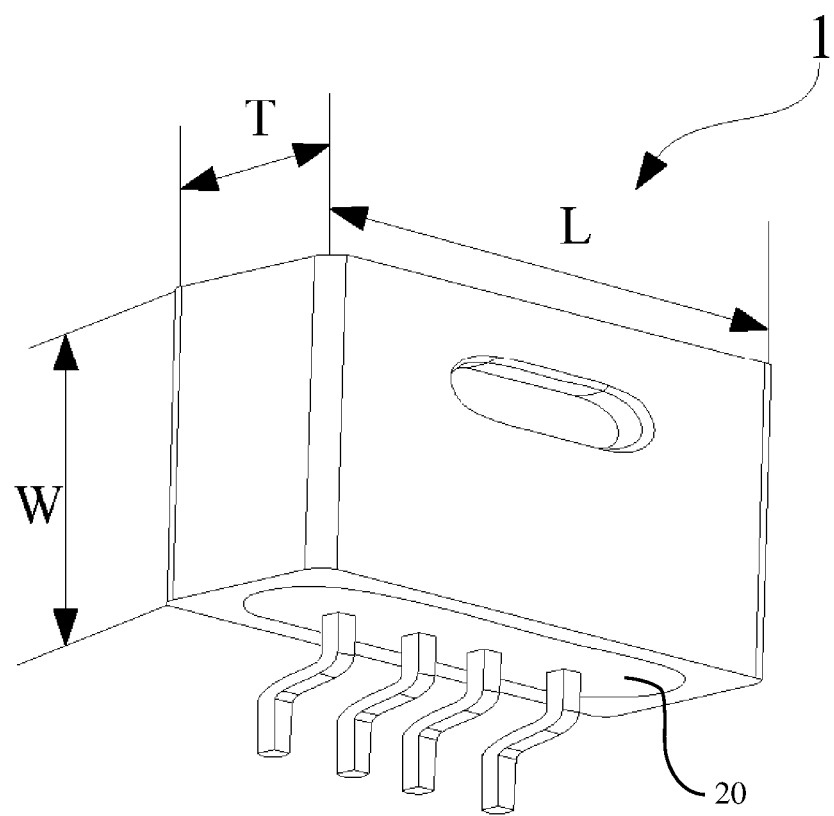
FIG. 1 is a stereogram of an explosion-proof miniaturized combustible gas sensor provided by the present invention.
Figure 2:
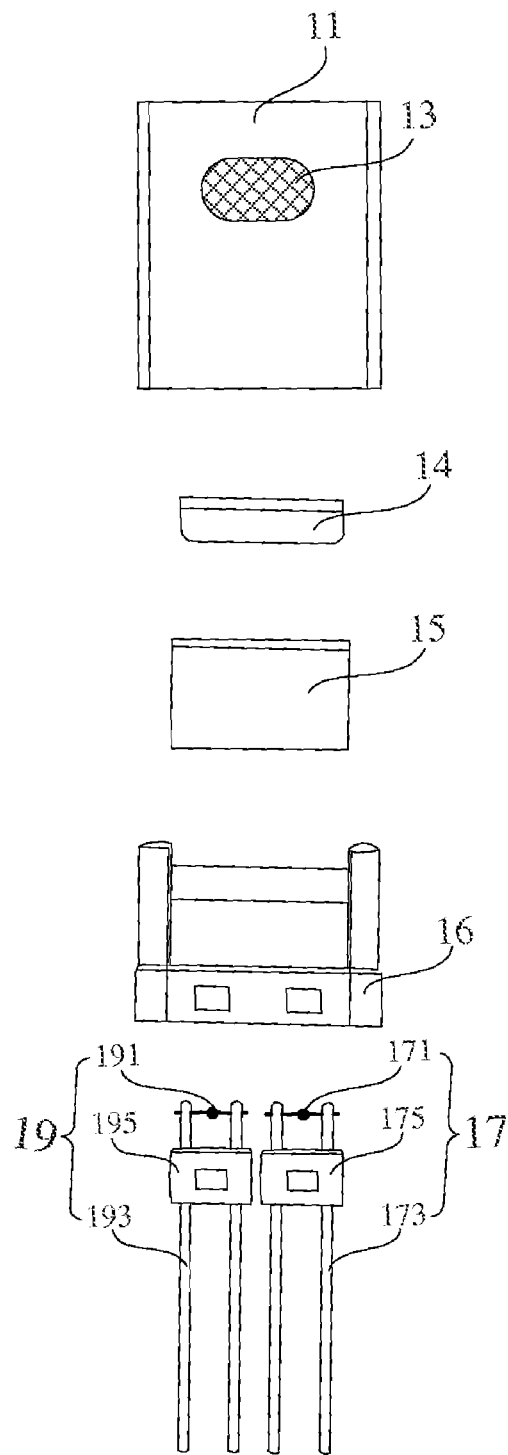
FIG. 2 is a structure breakdown diagram of the explosion-proof miniaturized combustible gas sensor provided by the present invention.

FIG. 1 and FIG. 2 show a stereogram and a structure breakdown diagram of an explosion-proof miniaturized combustible gas sensor provided by the present invention respectively. In combination with FIG. 1 and FIG. 2, the explosion-proof miniaturized combustible gas sensor 1 according to the present invention comprises: a metal casing 11, a wire mesh 13, a heat insulation module 15, a detection module 17, a compensation module 19 and a sealant.

Detailed depiction of the aforesaid components is as follows:

The metal casing 11 has an accommodation space therein. In this embodiment, the metal casing 11 is substantially of a hexahedral box shape, preferably, it is made of a stainless steel material and has a high strength and good heat dissipation performance. A surface of said metal casing 11 (e.g. bottom surface) defines an opening, such that said detection module 17, compensation module 19 and heat insulation module 15, etc. are placed into the accommodation space of said metal casing 11 via said opening, thereafter, said opening is sealed with said sealant. Further, an opening is provided on a side surface of the metal casing 11 perpendicular to said opening surface (this side surface is referred to as the front surface hereinafter), a wire mesh 13 is sintered at a position corresponding to said opening. In the present invention, a vertical surface perpendicular to said side surface where the wire mesh 13 is located and the other side surface opposite thereto serves as a transfer surface of a combustible gas (i.e. T shown in FIG. 1). It can be seen that the transfer surface of the combustible gas determines the overall height of the sensor. Wherein, the wire mesh 13 is connected to the accommodation space of said metal casing 11, which not only has the effect of allowing ventilation to enable a gas under detection to be transferred into the metal casing 11 via said wire mesh 13 for gas exchange, but also has a further protection effect to prevent a flame of the combustible gas to be transferred out to detonate the ambient environment. Preferably, the wire mesh 13 is a stainless wire mesh and the number of holes thereof can be set in accordance with the demand of the manufacturing process or the property of the combustible gas.

The heat insulation module 15 is embedded in the accommodation space of said metal casing 11 for heat insulation. In this embodiment, the heat insulation module 15 can be made by a thermal resistance material (e.g. plastic), and a thermal conductivity coefficient of said thermal resistance material is smaller than 0.6 w/(m·K). Said thermal resistance material is of a gas state, a liquid state or a solid state. When said thermal resistance material is of a solid state, the shape thereof can be a rod, a block, a sheet or even powder. On the one hand, in order to embed the heat insulation module 15 into the metal casing 11 effectively, the present invention further provides a clip 14 for fixing the heat insulation module 15, specifically, the clip 14 can be substantially of a Π shape to clamp the heat insulation module 15. On the other hand, in order to bond the heat insulation module 15 to the metal casing 11 more closely, a sealant is used (e.g. epoxy pouring) between the heat insulation module 15 and the metal casing 11 to connect the two and to seal any gap. Furthermore, on the one hand, a flange, a pole bolt or an extending portion, etc. can be arranged on an external wall of the heat insulation module 15 to enhance the bonding degree between the heat insulation module 15 and the metal casing 11. On the other hand, a seam allowance slot (not shown in the figure) in contact with said sealant is specially arranged on the inner wall of the metal casing 11, such that said sealant is embedded into said seam allowance slot during sealing to prevent rolling out of the sealant and to enhance the bonding degree of the sealing. In the present invention, the selected epoxy has a linear expansion coefficient of substantially $10^{-6}$ in./in./° C.~$10^{-5}$ in./in./° C., which is sufficiently close to that of the material of the heat insulation module 15 and is close to the linear expansion coefficient of the metal casing 11. In this way, even after a one-month-long extreme high and low temperature cycle (a high temperature of no lower than 95° C. and a low temperature of −410° C.) as prescribed in the explosion-proof authentication standard, a sufficient bonding strength between the sealant and the stainless casing can be maintained and no crack is generated. Even an explosive experiment cannot crack the metal casing 11 and the bonding strength is sufficient to resist the subsequent static hydraulic pressure test of as high as 4 MPa.

The present invention further provides a detection module 17 sensitive to a combustible gas and a compensation module 19 insensitive to a combustible gas. In actual application, the detection module 17 and the compensation module 19 can be fixed in the metal casing 11 through a fixing support but is not limited to this, for example, the detection module 17 and the compensation module 19 can also be coupled, nested or locked to each other to fix each other, thereby being fixed in the metal casing 11.

The detection module 17 is used to detect a combustible gas, said detection module 17 comprises: a detection element 171 assembled in said heat insulation module 15, a pair of detection pins 173 connected to two ends of said detection element 171 respectively and extending via said sealant from a side surface of said metal casing 11 and a detection pin frame 175 for supporting the pair of detection pins 173. The compensation module 19 is used to compensate influence on a signal of said detection module 17 caused by ambient temperature, humidity, pressure and airflow, etc.

The compensation module 19 comprises: a compensation element 191 assembled in said heat insulation module 15, a pair of compensation pins 193 connected to two ends of said compensation element 191 respectively and extending via said sealant from a side surface of said metal casing 11 and a compensation pin frame 195 for supporting the pair of compensation pins 193. Since the detection pins 173 and the compensation pins 193 configured on the detection module 17 and the compensation module 19 respectively extends from a side surface of the metal casing 11, as compared with the prior art of extending from a front surface or bottom surface, this design greatly reduces the overall thickness of a product and realizes miniaturization of a product.

The detection module 17 and the compensation module 19 are substantially identical in structure. A major difference between the two is: the detection element 171 of said detection module 17 has a higher combustible gas detection sensitivity than the compensation element 191 of said compensation module 19, that is, the detection element 171 of said detection module 17 has a relatively higher combustible gas detection sensitivity, while the compensation element 191 of said compensation module 19 has a relatively lower or even no combustible gas detection sensitivity. Herein, the combustible gas detection sensitivity refers to a change rate of a physical quantity or a chemical quantity indicating a change of a combustible gas along with a change of concentration of a combustible gas. In this embodiment, the detection element 171 comprises a noble metal carrying member and a ceramic material wrapping said noble metal carrying member, preferably, said noble metal carrying member is a Pt wire coil, said ceramic material further carries a simple substance or a compound sensitive to a combustible gas. The compensation element 191 comprises: a noble metal carrying member and a ceramic material wrapping said noble metal carrying member, preferably, said noble metal carrying member is a Pt wire coil. Obviously, the performance of the detection module 17 and performance of the compensation module 19 must be close enough in terms of thermal conductivity so that the compensation function can be realized. The closer their thermal conductivity performances are, the less the influence of the ambient temperature, humidity, pressure and airflow on the performance of the whole combustible gas sensor. However, the detection component and compensation component in an existing combustible gas sensor are usually not sufficiently matched due to the defect in structural design, thus, the existing combustible gas sensor has a performance far from ideal or requires extra compensation. The explosion-proof miniaturized combustible gas sensor provided by the present invention, however, takes this into full consideration in design: the detection module 17 and the compensation module 19 are designed as two independent hardware modules, and a pairing and matching operation is performed to the two modules in advance during manufacturing, upon completion of the matching operation, the two modules are transferred to the heat insulation module 15 for encapsulation, thereby avoiding the problem of poor compensation and enabling the compensation module 19 to compensate the influence of the ambient temperature, humidity, pressure and airflow, etc. on a signal of the detection module 17. In actual application, the resistance of the compensation module 19 matching said detection module 17 means a resistance of said compensation module 19 matching a resistance of said detection module 17 (e.g. resistance pairing to make the resistance values of the two equal or having a very small difference). Specifically, a ratio between the resistance of said detection module 17 and the resistance of said compensation module 19 ranges from 0.93 to 1.07, in some embodiments, a ratio between the resistance of said detection module 17 and the resistance of said compensation module 19 ranges from 0.983 to 1.020. Particularly, in the range of −40° C. to +70° C., a ratio between the resistance of said detection module and the resistance of said compensation module ranges from 0.975 to 1.013.

In order to encapsulate the detection module 17 and the compensation module 19 securely in the heat insulation module 15, the present invention further provides a fixing frame 16 for fixing the detection module 17 and the compensation module 19. In use, the fixing frame 16 is used as a connection device between the heat insulation module 15 and the detection module 17 and the compensation module 19. Specifically, one end of the fixing frame 16 is for accommodating the heat insulation module 15, and the other end of the fixing frame 16 is for accommodating the detection element 171 of said detection module 17 and the compensation element 191 of said compensation module 19. In actual application, said detection module and the compensation module are fixed in said sensor with a fixing support, or the detection module and the compensation module are coupled, nested or locked to each other to fix each other, thereby being fixed in the sensor.

The sealant 20 is used to encapsulate said heat insulation module 15, detection module 17 and compensation module 19 in the accommodation space of said metal casing 11. In the present invention, a bonding length (corresponding to W shown in FIG. 1) of said sealant 20 permeating into the accommodation space of said metal casing 11 is used as an effective bonding surface, said effective bonding surface is perpendicular to said transfer surface of the combustible gas. In this way, the effective bonding surface of said sealant and the transfer surface of the combustible gas do not influence each other, and the bonding, length required by the explosion-proof authentication (e.g, at least 3 mm) does not occupy the height of the sensor (that is, the distance of the transfer surface of the combustible gas), thereby, the overall height of a sensor is reduced and the metal casing 11 can be made into a flat box shape having a size as small as 14 mm*14 mm*5 mm (i.e. L*W*T in FIG. 1), wherein 5 mm is a thickness corresponding to the transfer surface of said combustible gas in said metal casing 11, which is much smaller than the height of usually no less than 8 mm of a traditional sensor.

An Example of Actual Application of a Sensor Disclosed by the Present Invention:

One type of the combustible gas sensor according to the present invention is a catalytic combustion combustible gas detector, and its working principle is: the detection element 171 in said detection module 17 has catalytic combustion activity to methane, while, the compensation element 191 in said compensation module 19 has no catalytic combustion activity or a relatively lower catalytic combustion activity to methane. Thus, when a combustible gas appears, the resistance of the detection element 171 increases and the resistance of the compensation element 191 decreases, remains unchanged or increases by a relatively smaller amplitude. Information about the relative change of the resistances of the two can be captured by means of the detection element 171 and the working element via a Wheatstone bridge, the information is associated with a concentration of the methane gas and a concentration value of the methane gas can be obtained through a pre-calibration process.

In summary, an explosion-proof miniaturized combustible gas sensor provided by the present invention comprises a metal casing, a wire mesh arranged on said metal casing, a heat insulation module embedded in said metal casing, a detection module and a compensation assembled in said heat insulation module and a sealant. Such a structure has the following advantages:

1. The transfer surface of the combustible gas is perpendicular to the effective bonding surface of the sealant such that the bonding length required by the explosion-proof authentication (e.g. at least 3 mm) does not occupy the height of the sensor, in this way, the overall height of the sensor can be reduced. Besides, since the detection pins and the compensation pins configured for the detection module and compensation module respectively extend from a side surface of the metal casing, as compared with the prior art of the pins extending from a front surface or bottom surface, the overall thickness of the product can be reduced greatly, thereby realizing the miniaturization of the product; furthermore, arranging a heat insulation module in the surrounding of the detection module and the compensation module can prevent heat loss due to a relative big gap between the two modules and the metal casing, in this way, the overall size of the sensor can be further reduced.

2. The present invention provides a detection module sensitive to a combustible gas and a compensation module insensitive to a combustible gas, and said detection module has a higher combustible gas detection sensitivity than said compensation module. Particularly, the detection module and the compensation module are made into two independent modules and a pairing and matching operation is performed to the two modules during manufacturing, encapsulation is performed after the matching (e.g. resistance matching to make the resistance values of the two equal or have a very small difference), thereby avoiding the problem of poor compensation and enabling said compensation module to compensate influence on a signal of said detection module caused by ambient temperature, humidity, pressure and airflow, etc.

3. A linear expansion coefficient of said selected sealant is $10^{-6}$ in./in./° C.~$10^{-5}$ in./in./° C., which is close to a linear expansion coefficient of stainless steel, thus, even after a one-month-long extreme high and low temperature cycle as prescribed in the explosion-proof authentication standard, a sufficient bonding strength between the sealant and the stainless casing can be maintained, which is sufficient to resist the subsequent static hydraulic pressure test of as high as 4 MPa.

The above embodiments are only for illustratively explaining the principle and effect of the present invention, rather than limiting the present invention. Any skilled person in the art can make modification(s) to the above embodiment without deviating from the spirit and scope of the present invention. Thus, the scope of protection of the present invention shall be defined as those listed in the Claims.

The invention claimed is:

1. An explosion-proof miniaturized combustible gas sensor comprising:
    a metal casing having an accommodation space therein:
    a wire mesh provided on a front vertical surface of said metal casing and in connection with said accommodation space for gas exchange such that a gas under detection is transferred into said metal casing via said wire mesh;
    a pair of vertical surfaces perpendicular to said front vertical surface where the wire mesh is located and a back vertical surface in a direction opposite the front vertical surface the direction being aligned as a transport direction of the combustible gas;
    a detection module sensitive to the combustible gas;
    a compensation module insensitive to the combustible gas, wherein said detection module and said compensation module have the same structure; wherein said detection module has a higher combustible gas detection sensitivity than said compensation module;
    a seam allowance slot around an opening in a horizontal bottom surface of the metal casing located perpendicular to the pair of vertical surfaces;
    a heat insulation module clamped to the detection module in the accommodation space of said metal casing;
    a sealant for embedding said heat insulation module, detection module and compensation module in the accommodation space and the seam allowance slot of said metal casing; wherein a bonding length of said sealant with said metal casing and the seam allowance slot in said accommodation space of said metal casing is used as a bonding surface, wherein said bonding surface is perpendicular to said transport direction of the combustible gas.

2. The explosion-proof miniaturized combustible gas sensor according to claim 1, wherein said detection module and said compensation module are fixed in said sensor via a fixing support, or said detection module and said compensation module are coupled, nested or locked to each other to fix each other, thereby being fixed in the sensor.

3. The explosion-proof miniaturized combustible gas sensor according to claim 1, wherein the detection module comprises: a detection element assembled in the heat insulation module and a pair of detection pins connected to two ends of the detection element respectively and extending via the sealant from a bottom surface of the metal casing; and wherein the compensation module comprises: a compensation element assembled in the heat insulation module and a pair of compensation pins connected to two ends of the compensation element respectively and extending via the sealant from a bottom surface of the metal casing.

4. The explosion-proof miniaturized combustible gas sensor according to claim 3, wherein the compensation element in said compensation module has a relatively lower combustible gas detection sensitivity, or even has no combustible gas detection sensitivity as compared with the detection element in said detection module.

5. The explosion-proof miniaturized combustible gas sensor according to claim 1 wherein the compensation module matching said detection module comprises a resistance of said compensation module matching a resistance of said detection module; in the range of −40° C. to +70° C., a ratio between the resistance of said detection module and the resistance of said compensation module ranges from 0.975 to 1.013.

6. The explosion-proof miniaturized combustible gas sensor according to claim 3, wherein said detection module further comprises a detection pin frame for supporting said pair of detection pins, said compensation module further comprises a compensation pin frame for supporting said pair of compensation pins.

7. The explosion-proof miniaturized combustible gas sensor according to claim 1, wherein said heat insulation module is composed of a thermal resistance material, a thermal conductivity coefficient of said thermal resistance material is smaller than 0.6 w/(m·K), and said thermal resistance material is of a gas state, a liquid state or a solid state.

8. The explosion-proof miniaturized combustible gas sensor according to claim 1, wherein a seam allowance slot in contact with said sealant is provided on an inner wall of said metal casing.

9. The explosion-proof miniaturized combustible gas sensor according to claim 1, wherein a linear expansion coefficient of said sealant is $10^{-6}$ in./in./° C.~$10^{-5}$ in./in./° C.

10. The explosion-proof miniaturized combustible gas sensor according to claim 1, wherein a surface of said metal casing comprises an opening, and said detection module, compensation module and heat insulation module are placed into the accommodation space of said metal casing via said opening, thereafter said opening is sealed with said sealant.

11. An explosion-proof miniaturized combustible gas sensor comprising:
 a metal casing having an accommodation space therein:
 a wire mesh provided on a front vertical surface of the metal casing and in connection with the accommodation space for gas exchange such that a gas under detection is transferred into the metal casing via the wire mesh;
 a pair of vertical surfaces perpendicular to the front vertical surface where the wire mesh is located and back vertical surface opposite thereto;
 a detection module sensitive to the combustible gas;
 a compensation module insensitive to the combustible gas, wherein the detection module and the compensation module have the same structure;
 wherein the wire mesh is aligned with the detection module and the compensation module in the transport direction;
 a seam allowance slot around an opening in a horizontal bottom surface of the metal casing located perpendicular to the pair of vertical surfaces;
 a heat insulation module clamped to the detection module in the accommodation space of said metal casing;
 a sealant for embedding the heat insulation module, detection module and compensation module in the accommodation space and the seam allowance slot of the metal casing; wherein a bonding length of said sealant with said metal casing and the seam allowance in said accommodation space of said metal casing is used as a bonding surface, wherein said bonding surface is aligned perpendicular to said transport direction of the combustible gas.

12. The explosion-proof miniaturized combustible gas sensor according to claim 11, wherein the detection module and the compensation module are fixed in the sensor via a fixing support, or the detection module and the compensation module are coupled, nested or locked to each other to fix each other, thereby being fixed in the sensor.

13. The explosion-proof miniaturized combustible gas sensor according to claim 1, wherein the detection module comprises: a detection element assembled in the heat insulation module and a pair of detection pins connected to two ends of the detection element respectively and extending via the sealant from a bottom surface of the metal casing; and wherein the compensation module comprises: a compensation element assembled in the heat insulation module and a pair of compensation pins connected to two ends of the compensation element respectively and extending via the sealant from a bottom surface of the metal casing.

14. The explosion-proof miniaturized combustible gas sensor according to claim 13, wherein the compensation element in the compensation module has a relatively lower combustible gas detection sensitivity, or even has no combustible gas detection sensitivity as compared with the detection element in the detection module.

15. The explosion-proof miniaturized combustible gas sensor according to claim 13, wherein the detection module further comprises a detection pin frame for supporting the pair of detection pins, the compensation module further comprises a compensation pin frame for supporting the pair of compensation pins.

16. The explosion-proof miniaturized combustible gas sensor according to claim 11 wherein the compensation module matching said detection module comprises a resistance of said compensation module matching a resistance of said detection module; in the range of −40° C. to +70° C., a ratio between the resistance of said detection module and the resistance of said compensation module ranges from 0.975 to 1.013.

17. The explosion-proof miniaturized combustible gas sensor according to claim 11, wherein the heat insulation module is composed of a thermal resistance material, a thermal conductivity coefficient of the thermal resistance material is smaller than 0.6 W/(m·K), and the thermal resistance material is of a gas state, a liquid state or a solid state.

18. The explosion-proof miniaturized combustible gas sensor according to claim 11, wherein a seam allowance slot in contact with the sealant is provided on an inner wall of the metal casing.

19. The explosion-proof miniaturized combustible gas sensor according to claim 11, wherein a linear expansion coefficient of the sealant is $10^{-6}$ in./in./° C.~$10^{-5}$ in./in./° C.

20. The explosion-proof miniaturized combustible gas sensor according to claim 11, wherein a surface of the metal casing comprises an opening, and the detection module, compensation module and heat insulation module are placed into the accommodation space of the metal casing via the opening, thereafter the opening is sealed with the sealant.

* * * * *

UNITED STATES PATENT AND TRADEMARK OFFICE
CERTIFICATE OF CORRECTION

PATENT NO. : 9,778,217 B2
APPLICATION NO. : 14/432092
DATED : October 3, 2017
INVENTOR(S) : Fuxia Liu and Aimin Su It is certified that error appears in the above-identified patent and that said Letters Patent is hereby corrected as shown below:

On the Title Page

Page (2), References Cited, Column 2, Line 1: insert --et al.-- after "Schlichte"

Page (2), References Cited, Column 2, Line 9: insert --et al.-- after "Schlichte"

Page (2), References Cited, Column 2, Line 11: insert --et al.-- after "Schlichte"

In the Specification

Column 6/Line 42: "-410°" should be "-40°"

In the Claims

Column 11/Line 49: "claim 1" should be "claim 11"

Signed and Sealed this
Second Day of January, 2018

Joseph Matal
*Performing the Functions and Duties of the*
*Under Secretary of Commerce for Intellectual Property and*
*Director of the United States Patent and Trademark Office*